(12) United States Patent
Mølster

(10) Patent No.: US 6,289,545 B1
(45) Date of Patent: *Sep. 18, 2001

(54) DEVICE FOR CLEANING WITHIN THE ORAL CAVITY

(76) Inventor: Olav Mølster, Boks 503, N-6901 Floro (NO)

( * ) Notice: Subject to any disclaimer, the term of this patent is extended or adjusted under 35 U.S.C. 154(b) by 0 days.

This patent is subject to a terminal disclaimer.

(21) Appl. No.: 09/254,361
(22) PCT Filed: Sep. 4, 1997
(86) PCT No.: PCT/NO97/00233
  § 371 Date: Apr. 16, 1999
  § 102(e) Date: Apr. 16, 1999
(87) PCT Pub. No.: WO98/09573
  PCT Pub. Date: Mar. 12, 1998

(30) Foreign Application Priority Data

Sep. 5, 1996 (NO) .................................................. 963699

(51) Int. Cl.[7] .................................................. A46B 9/04
(52) U.S. Cl. .................................................. 15/167.1; 15/111
(58) Field of Search .................................................. 15/167.1, 111

(56) References Cited

U.S. PATENT DOCUMENTS

| | | | |
|---|---|---|---|
| 36,309 | * | 8/1862 | Schweizer . |
| 697,336 | * | 4/1902 | Hagerty . |
| 1,658,706 | * | 2/1928 | Carrott . |
| 4,455,704 | * | 6/1984 | Williams . |
| 5,048,143 | * | 9/1991 | Carroll .................. 15/167.1 |
| 5,067,195 | * | 11/1991 | Sussman ............... 15/167.1 |
| 5,175,901 | * | 1/1993 | Rabinowitz ........... 15/167.1 |
| 5,511,273 | * | 4/1996 | Carroll .................. 15/167.1 |
| 5,709,004 | * | 1/1998 | Paduano ............... 15/167.1 |

FOREIGN PATENT DOCUMENTS

| | | | | |
|---|---|---|---|---|
| 16979 | * | 9/1894 | (GB) ................... | 15/167.1 |
| 0021620 | * | 11/1894 | (GB) ................... | 15/167.1 |
| 179950 | * | 3/1923 | (GB) ................... | 15/167.1 |
| 0449836 | * | 7/1936 | (GB) ................... | 15/167.1 |
| 773038 | * | 4/1957 | (GB) . | |
| 90/02498 | * | 3/1990 | (WO) ................. | 15/167.1 |

* cited by examiner

*Primary Examiner*—Randall E. Chin
(74) *Attorney, Agent, or Firm*—Francis C. Hand, Esq.; Carella Byrne Bain Gilfillan Cecchi Stewart & Olstein

(57) ABSTRACT

The device for cleaning the inside of an oral cavity includes a cleaning member having bristles on an upper surface for brushing purposes and a scraping edge extending along a rear edge of a lower surface for scraping the tongue and/or interior surfaces of an oral cavity. The scraping edge is formed by an upstanding ridge which extends from the lower surface a distance of from 1 to 3 millimeters. In some embodiments, the cleaning member may be straight while other embodiments the cleaning member may be bowed. Also, the cleaning instrument may have a single handle for holding the cleaning member or a pair of handles.

11 Claims, 8 Drawing Sheets

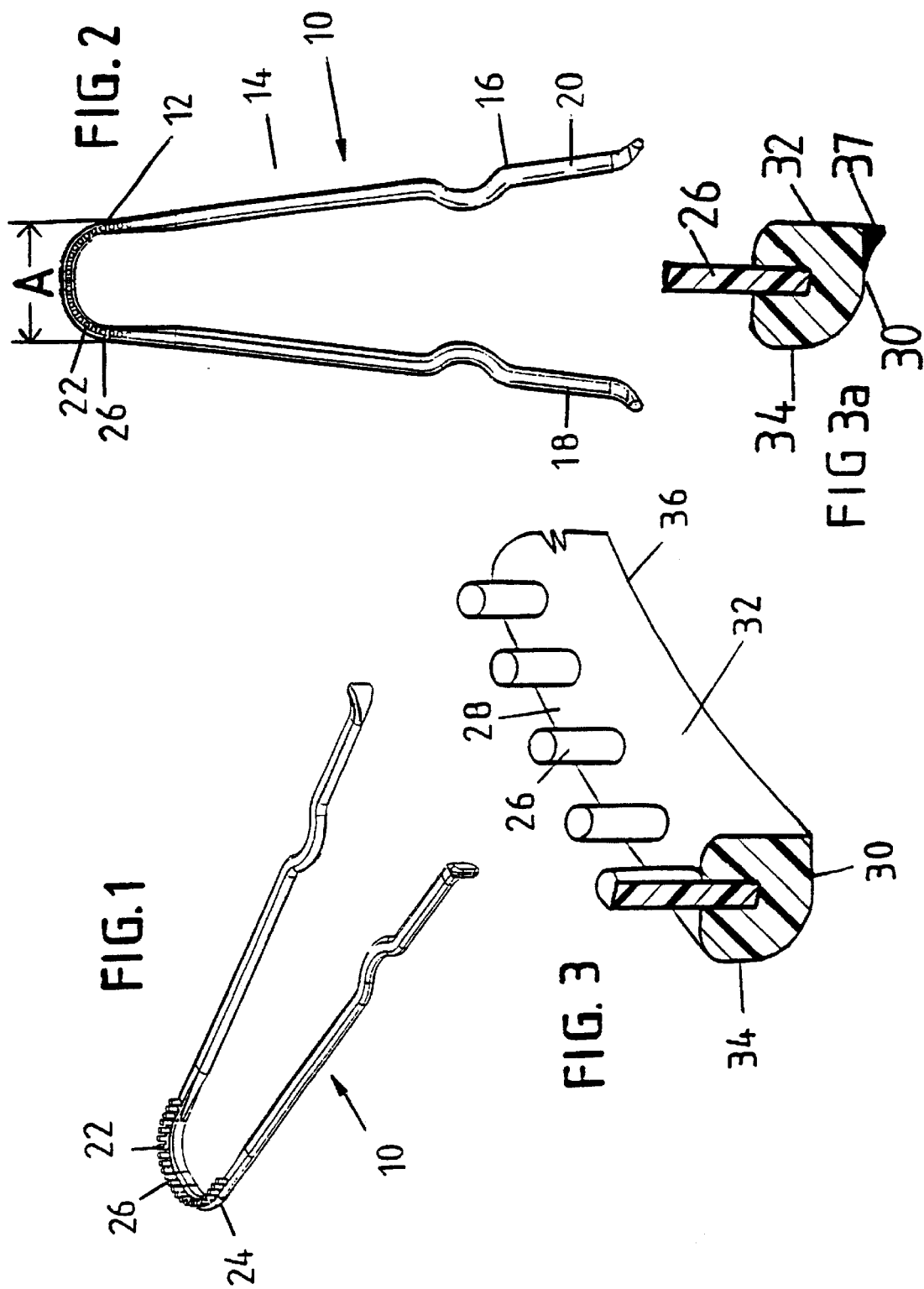

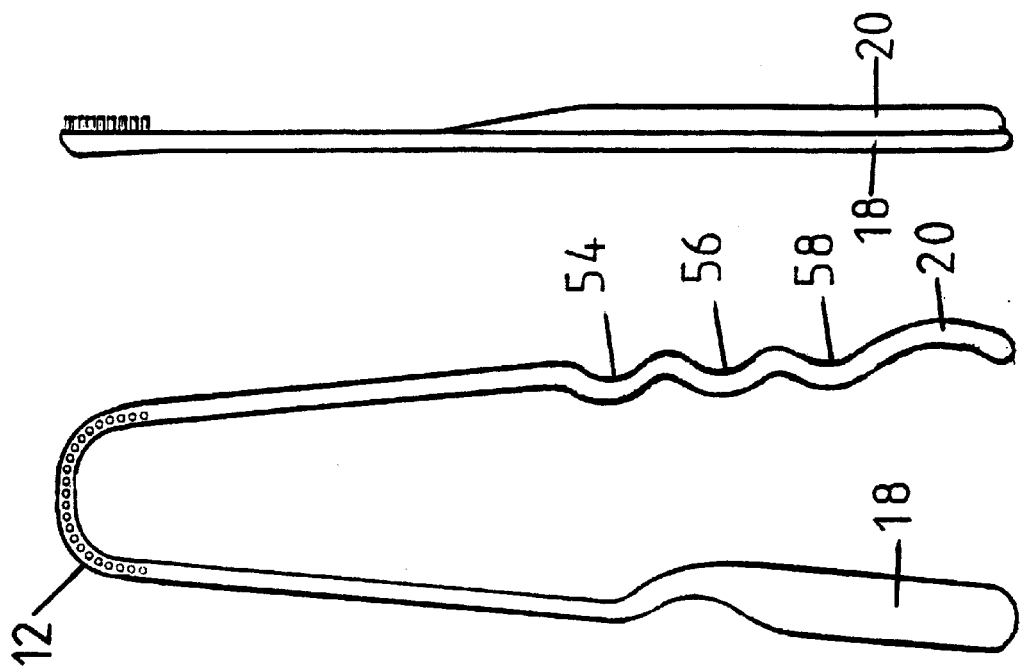
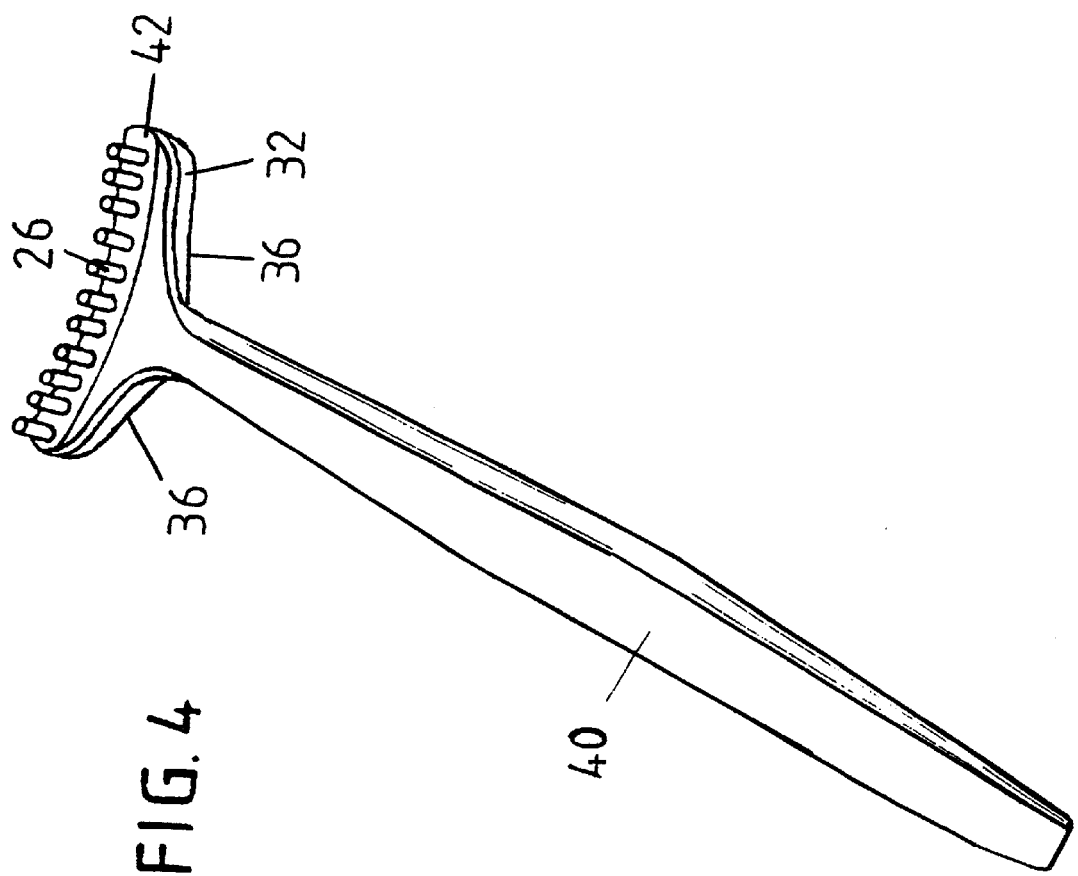

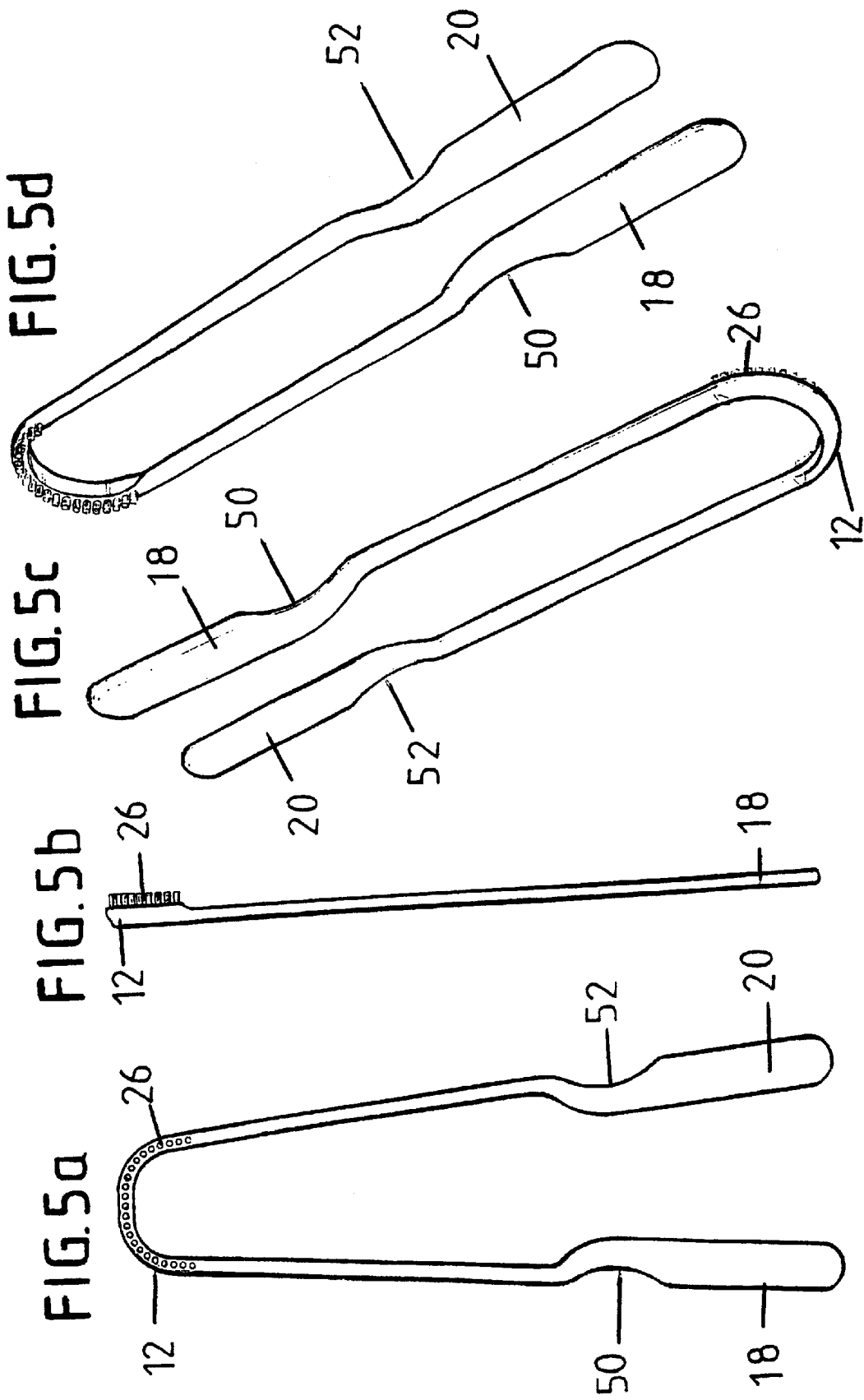

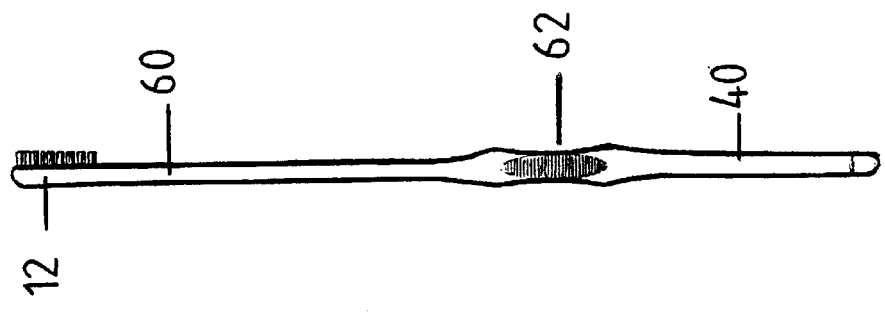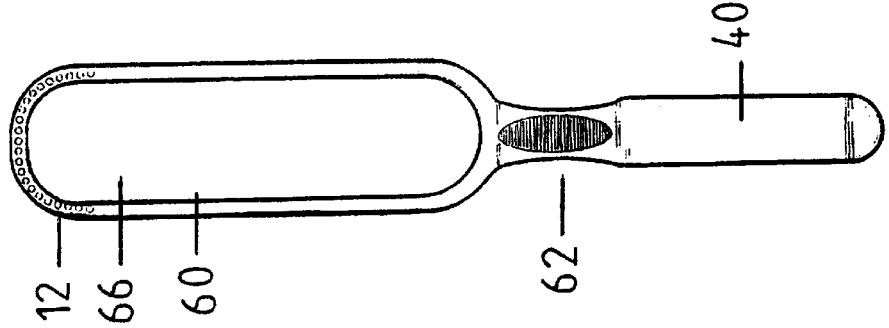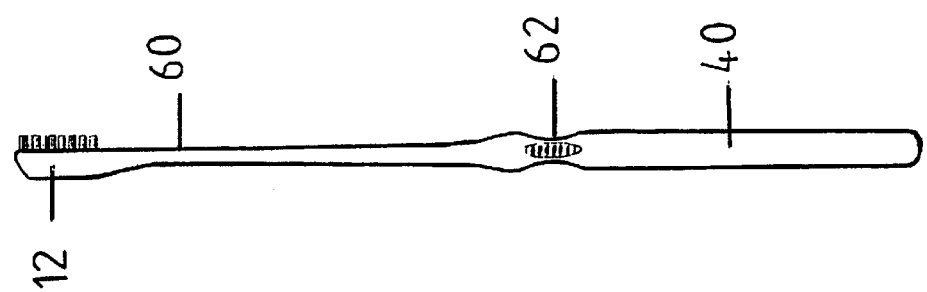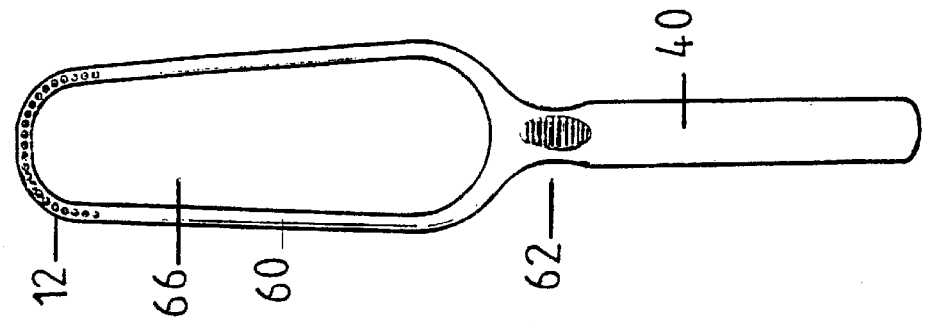

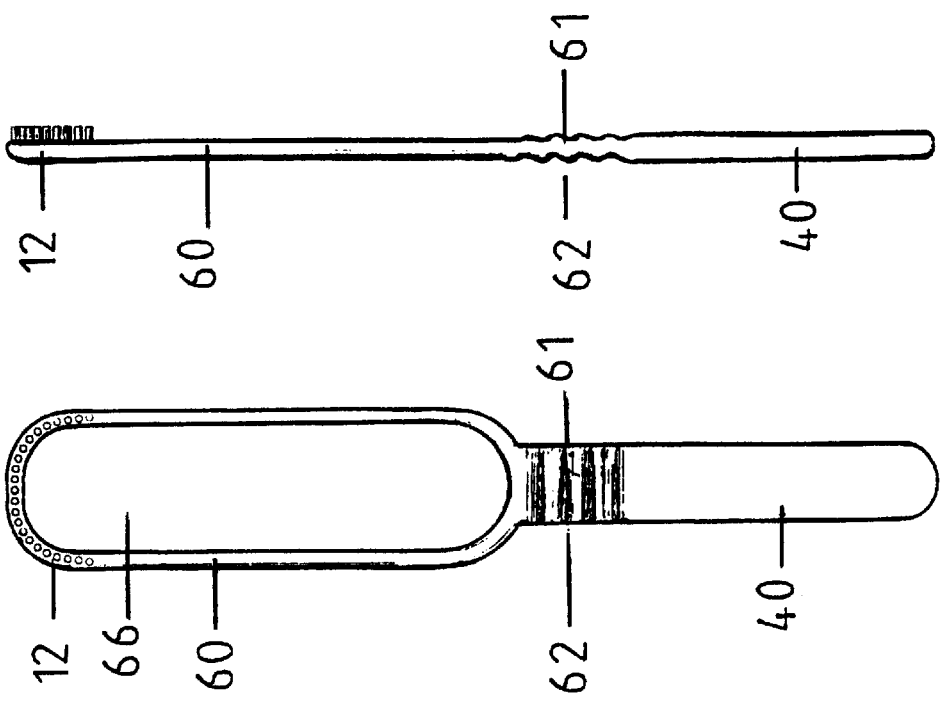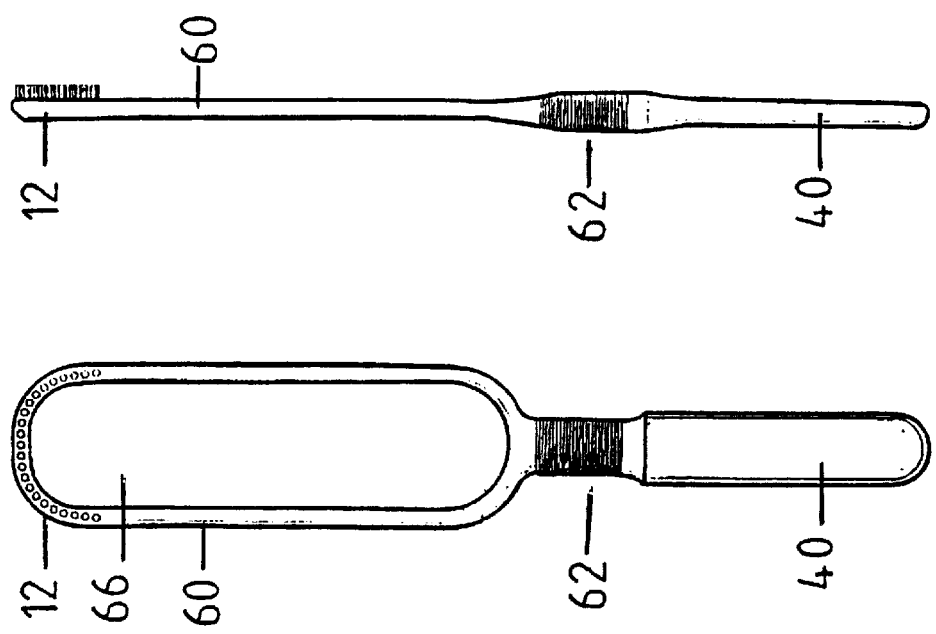

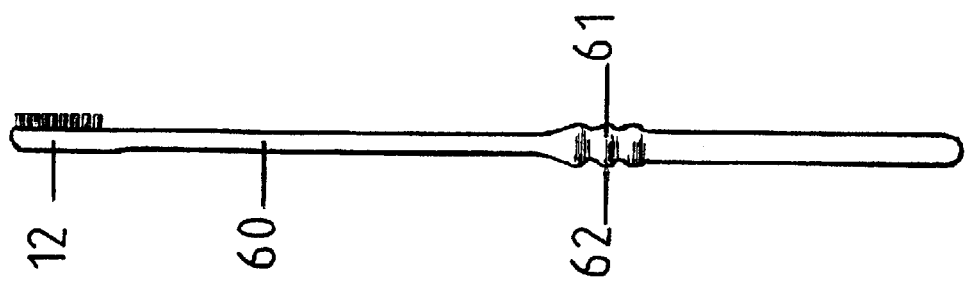
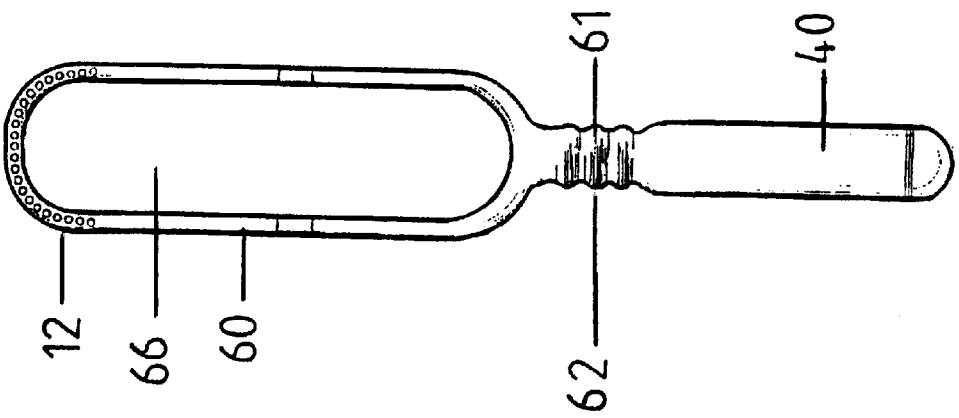
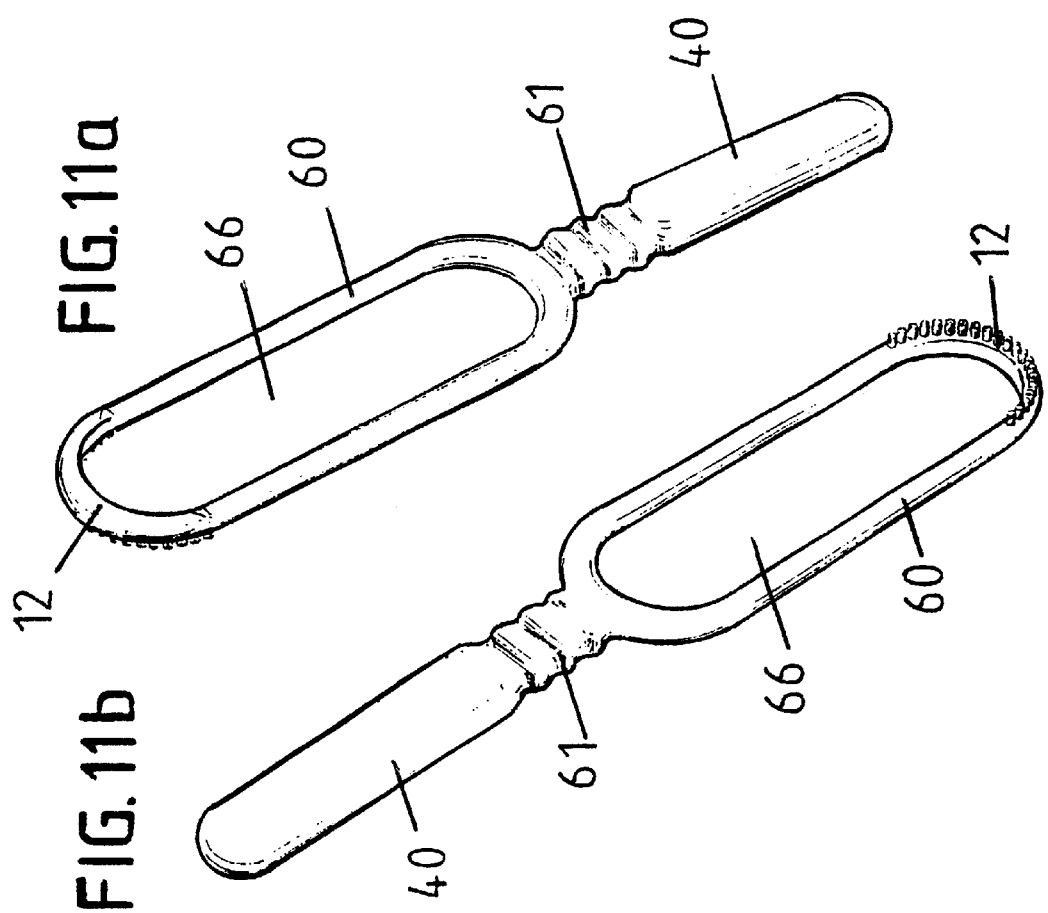

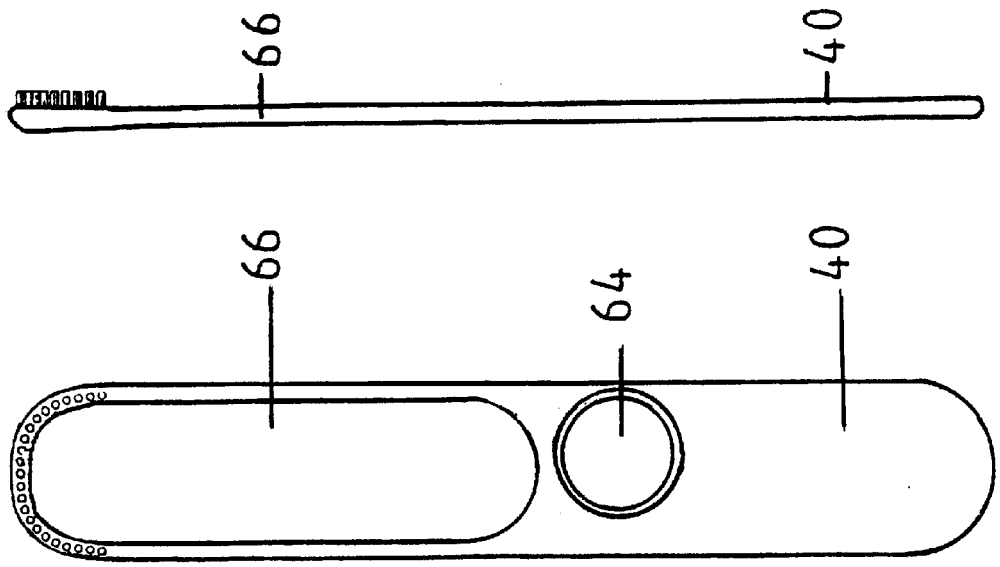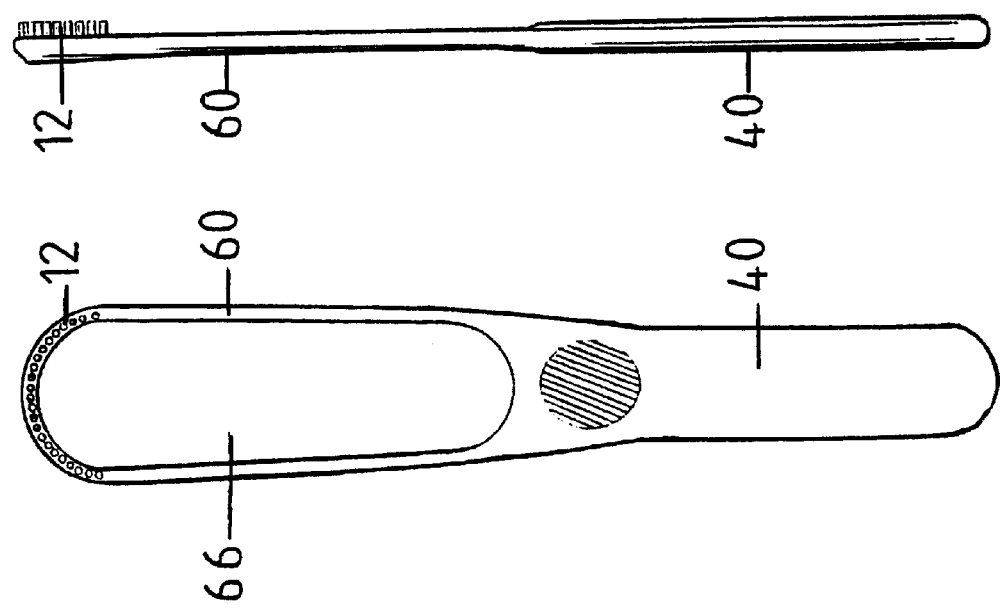

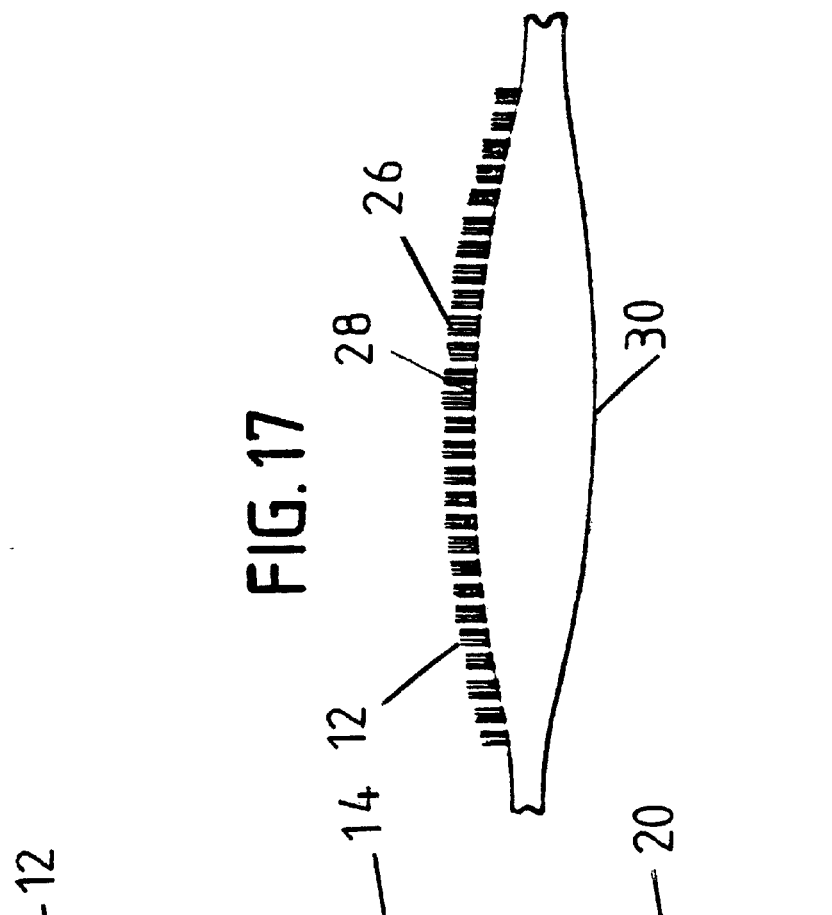
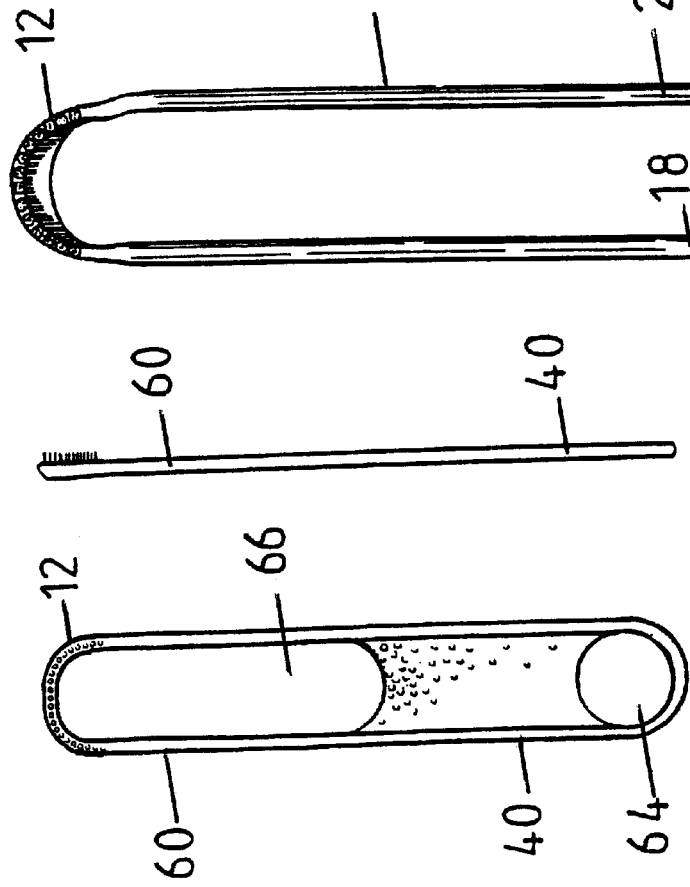

DEVICE FOR CLEANING WITHIN THE ORAL CAVITY

The present invention relates to a device for cleaning of the oral cavity.

With the present invention the aim is to alleviate the problem which many people have with bad breath.

The oral cavity (cavum oris) consists of teeth, cheeks, soft palate, tongue, mouth floor, transition folds and cheek mucous membranes. All these components can collect bacteria-plaque, food residues and dead skin cells. With toothless people, the roof of the mouth/the palate and floor of the mouth including the lower jaw (mandibula) can be sites for this collection of material. Several investigations have shown that thorough cleaning of the tongue and particularly its rear portions will reduce the afore-mentioned frequency of bad breath, will increase the sense of taste and will have the effect of refreshing the oral cavity. Thorough cleaning of the teeth is normal to-day in the population, but large geographical and social variations exist. The western world is to-day little focussed on other than the brushing of teeth and interdental cleaning with tooth floss and tooth picks. The phenomenon of bad breath can stem from the afore-mentioned conditions, but a series of research workers have published investigations where the main problem is the rear portions of the tongue. As regards persons without teeth, collections of dead skin cells, fungi and bacteria will not only occur in the prosthesis itself, but also in cheeks and portions of the palate. It is also known that dead skin cells in the mucous membranes can influence the aroma of the air from exhalation.

A series of instruments are known for the removal of accumulations of odor forming material on the tongue, and reference shall be made here to GB-patent specifications 2.027.347, 2,234.903, 2.260.905 and 2.265.831. These patent specifications show a U-shaped bow which comprises a scraping edge and two handles which the user grips on, after which he can scrape the tongue with the scraping edge of the bow. However this scraping does not give a sufficient cleaning of the tongue and there is no discussion either of cleaning portions of the oral cavity as is mentioned above. In addition a cleaning instrument is known from U.S. Pat. No. 1,891,864 which comprises a combination of bristles and scraping edge. This instrument is however large and broad and long and it comprises up to six rows of bristles. It will therefore occupy a relatively large space in the oral cavity and there is the danger that the user gets vomiting feelings. The scraping edge which in the patent is shown by the reference number 4, is constituted by a separate metal plate, and it appears to consist of a sharp edge, which in itself can lead to the tongue being cut or injured.

It is therefore an object of the present invention to produce a new instrument for cleaning of the oral cavity, and which remedies the drawbacks which are outlined above for the known cleaning instruments.

Briefly, the invention is directed to a cleaning instrument for an oral cavity comprising a bow-shaped cleaning element having oppositely disposed convex surfaces to define an approximately cigar-shape and a scraping edge along one side thereof. In addition, the cleaning instrument has at least one row of bristles mounted on the cleaning element along a second side opposite the scraping edge side of the cleaning element as well as a handle member which is connected with the cleaning element for manual grasping of the cleaning instrument.

According to the invention the device is used for the cleaning of the tongue, the mucous membranes, and if necessary, the palate portion within the oral cavity It is preferred to use the device together with a cleaning agent, such as a paste, gel or mouthrinse to be placed on the bristles.

Advantages and details concerning the instrument according to the present invention shall now be explained further with reference to the enclosed Figures, wherein:

FIGS. 1 and 2 show respectively a perspective view and a plan view of a preferred construction of the instrument according to the present invention;

FIG. 3 shows a cross-section, partly in perspective, of the bristle-carrying portion of the instrument;

FIG. 3a shows a cross-section of an alternative design of the scraping edge of the bristle-carrying portion of the instrument;

FIG. 4 shows an alternative construction of a cleaning instrument according to the invention;

FIG. 5a illustrates a modified cleaning instrument employing finger-receiving recesses in the handle member;

FIG. 5b illustrates a side view of the cleaning instrument of FIG. 5a;

FIG. 5c illustrates a bottom view of the cleaning instrument of FIG. 5a;

FIG. 5d illustrates a perspective view of the cleaning instrument of FIG. 5a;

FIG. 6a illustrates an alternative construction of a cleaning instrument employing a plurality of finger-receiving recesses in a two-legged handle member;

FIG. 6b illustrates a side view of the cleaning instrument of FIG. 6a;

FIG. 7a illustrates an alternative construction of a cleaning instrument having a handle member of one-piece construction;

FIG. 7b illustrates a sideview of the cleaning instrument of FIG. 7a;

FIG. 8a illustrates a variation of the cleaning instrument of FIG. 7a;

FIG. 8b illustrates a sideview of the cleaning instrument of the FIG. 8a;

FIG. 9a illustrates a further variant of the cleaning instrument of FIG. 7a;

FIG. 9b illustrates a sideview of the cleaning instrument of FIG. 9a;

FIG. 10a illustrates a further variant of the cleaning instrument of FIG. 7a;

FIG. 10b illustrates a sideview of the cleaning instrument of FIG. 10a;

FIG. 11a illustrates a perspective view of a further variant of the cleaning instrument of FIG. 7a;

FIG. 11b illustrates a bottom perspective view of the cleaning instrument of FIG. 11a;

FIG. 12a illustrates a variant of the cleaning instrument similar to FIG. 11b;

FIG. 12b illustrates a sideview of the cleaning instrument of FIG. 12a;

FIG. 13a illustrates a cleaning instrument of slightly tapered construction in accordance with the invention;

FIG. 13b illustrates a sideview of the cleaning instrument of FIG. 13a;

FIG. 14a illustrates a cleaning element having a finger hole in a handle member in accordance with the invention;

FIG. 14b illustrates a sideview of the cleaning instrument of FIG. 14a;

FIG. 15a illustrates a variant of the cleaning instrument of FIG. 14a;

FIG. 15b illustrates a sideview of the cleaning instrument of FIG. 15a;

FIG. 16 shows an alternative and preferred construction of the head part of the instrument.

FIG. 17 shows a side view of the head part of the instrument according to FIG. 16.

An instrument according to the present invention for cleaning different parts of the oral cavity is shown in FIGS. 1 and 2 by the reference numeral 10. The instrument comprises three main components, a front cleaning member 12, a middle section 14, and a rear handle member 16 (a shaft). The middle section 14 connects the cleaning member and the handle member 16 (the shaft).

The cleaning member 12 of the instrument 10 preferably forms a bow-shaped U-shaped bow profile, where each of the legs of the U shape is further connected, via the middle section 14, to the respective elongate handle parts 18, 20. The handle parts (the legs) 18, 20 are essentially designed so that the instrument can be gripped by the user's own hand with the thumb about the one leg 18 is of the handle, while the other fingers are laid about the other handle 20.

The U-shaped bow-cleaning member 12 further comprises a first (bristle-carrying) side surface 22 and a second (scraping element-carrying) side surface 24. The first and second side surfaces 22 and 24 are substantially oppositely directed when looking in towards the belly part or back part of the bow (U-shape) according to FIG. 1, and form planes which are substantially parallel to the directions of the handles (the shafts) 18, 20. The row of bristles 26 can be imbedded in the side surface, if desired be pressed into holes which are punched out in the side surface of the bow member.

The cross-section for the rod/bow can be square or rectangular with rounded corners, or can be circular, oval or the rod can have a composite cross-section of these With reference to FIG. 3, the bow member comprises the first (bristle-carrying) side surface 28, and the second (scraper element-carrying) side surface 30, these side surfaces being substantially oppositely directed. The wall-surface (belly side) 32 which faces inside the U-shape of the bow, and the wall surface 34 (back side) facing out of the U, connect respectively the two side surfaces 28 and 30. The side surfaces 28 and 30 form generally a right angle with the belly and back sides, but the elongate edge between the surfaces is rounded. The elongate edge which is defined between/by the belly surface 32 and the second side surface 30, form scraping edge 36 of the instrument. The two scraping edge-forming surfaces, namely the belly surface 32 and the second surface 30 can besides form dissimilar angles with each other, and the longitudinal edge 36 which is formed between them, will then have varying sharpness dependent upon what the angle is between the surfaces 30 and 32. Obviously the sharpness is also regulated by the rounding of the edge 36. The edge 36 must be so much rounded that the user does not cut himself in the tongue, in the skin or the mucous membranes when he draws in normal fashion the instrument over the tongue in order to perform the scraping. FIG. 3 shows the preferred cross-sectional profile of the rod which forms the cleaning member 12. The rear side 34 and the second side surface 30 form together an arcuate shape, and preferably an approximately circular cross-section.

According to another preferred embodiment of the device of the invention, which appear on FIG. 3a, the scraping edge is defined by a ridge 37 formed at the second side surface 30 and an extension of the belly side 32, said ridge being elevated upwardly from said surface and extends along the arcuate shape of the bow. The ridge may be elevated from the surface in range of approximately 1–3 millimeters. The ridge top edge (i.e. APEX) is rounded in order not to effect cut injuries in the tongue in use.

The bristles 26 are installed as a row of bristles in the first side surface 28. The rows of bristles consists of a number of bundles of bristles which are each imbedded or pressed down in holes in the bow. The bristles 26 can be up to 8 mm. (millimeters) high, but preferably have a height of 3 mm., and can consist of bristles of dissimilar hardness. In the FIGS. 1–3 a cleaning instrument is shown having one row of bristles, but two rows of bundles of bristles can also be used.

The distance or breadth between the outer edges of the front cleaning member 12 (or head portion) is denoted A on FIG. 2. The instrument according to the invention can be made with dissimilar breadths A adapted for adults and children. For an adult person the cleaning member 12 is made with a breadth of about 2.5–4 cm. something which approximately corresponds to the breadth of the tongue at the root of the tongue with an adult person. For children a breadth A of 2–2.5 cm may be suitable. An universal instrument intended for both children and adults way have a breadth (A) of 2–3 cm.

In FIG. 4 an alternative construction of the cleaning instrument according to the invention is shown. According to this alternative the instrument comprises only one handle 40, designed approximately as a conventional toothbrush. The one end of the handle 40 is connected to a transverse head portion 42 which then constitutes the cleaning member 12. The cleaning member has generally the same design with respect to the bristles 26, the scraping edge 36, the cross-sectional form, and the breadth as shown in FIGS. 1–3 and discussed above. According to an alternative embodiment the head portion can be totally straight, as is indicated in FIG. 4. The handle is fastened midway between outer ends of the head portion 42.

According to an alternative construction both side surfaces 28 and 30 can be provided with a row of bristles. In order that the one edge shall function as a scraping edge the type of bristle installed ought then to be of a somewhat harder type than the row of bristles 26 on the opposite edge. This means that the instrument according to the invention can be equipped with separate rows of bristles having different softnesses.

There shall now be outlined how the cleaning instrument according co the invention is to be used.

The instrument 10 in gripped by the hand of the user and is guided backwards to the back portions of the tongue with the bristles 26 facing towards the rear of the tongue. Some scrubbing movements are undertaken forwards and backwards in the longitudinal direction of the tongue in order to loosen the material from the surface of the tongue, and that which sits in depth. In order to achieve a satisfactory scrubbing the instrument must be pressed down against the tongue with a given force.

Thereafter the instrument is taken out of the mouth, and it is turned so that the scraping edge faces towards the surface of the tongue. Again the instrument is guided backwards to the back portions of the tongue. With a given pressure, a scraping of the tongue is undertaken by drawing the utensil from the back portions of the tongue and forwards to the front portion (the tip of the tongue). This operation is repeated four or five times, and one will then be able to see that a series of slime/plaque/bacteria has collected in the front portions of the tongue or that it lies as a coating on the scraping edge. This material is rinsed out of the mouth with clean water from the tap.

Thereafter, the instrument is guided inside the mouth again, and now with the working bristles against the cheek mucous membranes on the right and then on the left side The working edge is drawn thereafter 3–4 times from the back portions at the wisdom tooth region towards the corner of the mouth. This operation is repeated correspondingly on the opposite side.

During the scrubbing it is preferred that a cleaning agent is used. This can be placed on the tongue before the scrubbing with the bristles starts. Alternatively the cleaning agent can be placed on the row of bristles whereby it is scrubbed out over of the surface of the tongue. The cleaning agent can comprise a paste, gel, powder or have another suitable consistency. A paste can for example comprise conventional toothpaste from a tube and which is squeezed out and placed as a stripe up on or down in the row of bristles. Then it is ensured that the paste is spread satisfactorily out over the tongue.

With persons who do not have teeth, one is also able to utilise the inventive instrument to clean the palate portion. The bristles are guided backwards to the transition between the hard and the soft palate, and one brushes forwards and to the side with small scrubbing movements.

The FIGS. 5a–b, 5c–d, and 6 show three constructions where the cleaning head portion is roughly the same as discussed previously in connection with the FIGS. 1–2, while the difference lies mainly in the design of the handle member 16.

FIGS. 5a–b show a variant of an instrument according to the invention in a plan view and a side view respectively, while FIGS. 5c–d shows perspective views seen from above and below respectively of the instrument.

According to the construction of FIGS. 5a–b and 5c–d the handle legs 18, 20 are broader in the plane section than the middle piece 14 and the head member 12. Further the handle legs 18, 20 comprise like designed and laterally (from each other) directed concavities 50–52, where a person places the thumb and the forefinger during use of the instrument. The FIGS. 5a–b and 5c–d respectively show two variants of each other, the differences in these lying in the head portion. In the construction according to FIGS. 5a–b the shorter front bristle-carrying portion is approximately rectilinear, while in the construction according to FIGS. 5c–d the head portion forms approximately a semi-circle.

According to FIGS. 6a and 6b, the right handle leg 20 is fashioned having a wave-shaped design with concavities 54, 56, 58 adapted for the placing of the user's fore, middle and ring fingers. This solution will give a still better control in the use of the instrument.

FIGS. 7–12 show examples of cleaning instruments according to the invention comprising one legged handles, and where the middle piece 14 and the cleaning head 12 have generally the same form as the example according to FIGS. 1–2. The middle piece 14 and the cleaning head form a bow-shaped oblong closed ring 60 one end of which comprises the head member 12, while the other end extends over into the handle 40 in a transition region 62.

The transition region 62 between the middle portion 60 and the handle member is in plan view designed with concave sides, so that there are formed one or more ring-shaped neck portion-forming grooves in the transition portion. The whole or parts of the groove can be designed with a rough surface. When the user grips the handle with his thumb and forefinger placed on each side of the neck is portion, and against the rough surfaces, this gives a better grip. In the handle there can also be designed a number of small depressions, or a number of small elevations (warts) in the surface for improving the gripping characteristics of the handle.

FIGS. 7a and 7b show a construction where the legs or the middle piece 60 converges/tapers off somewhat forwards towards the head portion, and where in the neck portion there are formed a number of rough portions round the periphery of the neck portion.

FIGS. 8a and 8b show an embodiment where the legs of the middle piece 60 extends straight forwards towards the arcuate head portion 12, and where the tapered neck portion, which is formed with a number of rough portions around the periphery of the neck portion, has a somewhat larger longitudinal dimension than the example according to FIG. 7a.

FIGS. 9a and 9b show a construction where the legs of the middle piece 60 extends straight forwards towards the arcuate head portion 12, and where the whole of the tapered neck portion 62 is formed as a rough portion around the periphery of the neck portion, and has a length corresponding to the example according to FIG. 8a.

The example according to FIGS. 10a and 10b does not comprise any tapered neck portion in the transition between the handle member 40 and the middle portion, as the previous examples. This example comprises instead several coarse grooves 61 in the upper and under side, that is to say in the middle portion which defines that region where the thumb and forefinger are placed. In this construction also the legs of the middle piece 60 extend straight forwards towards the arcuate head portion 12.

FIGS. 11a and 11b show two perspective views (obliquely from above and below respectively) of a variant of the cleaning instrument according to FIG. 10a, the grooves 61 extending here around the whole of this part of the shaft 40 or the handle member 40. Further the shaft 40 is somewhat narrower than in the construction of FIG. 10a.

FIGS. 12a and 12b show a similar construction of the cleaning instrument corresponding to FIG. 10a, but where the marked tapered neck portion from the previously discussed solutions is retained. In this construction the shaft 40 is still somewhat narrower than in the construction according to FIG. 11a.

FIGS. 13a and 13b show a construction where the handle element extends with a gradually greater breadth towards the middle portion 60 which in turn becomes gradually broader (diverges) forwards towards the head portion. The arcuate head portion 12 with the row of bristles 26 is designed as in the former examples.

FIGS. 14a and 14b and FIGS. 15a and 15b show two constructions where the middle portion 60 extends directly over into the handle element 40, and where these are equally broad, that is to say that side edges of the instrument extend in parallel. According to the example of FIG. 14a the handle 40 comprises a through round hole 64 at the transition to the middle portion 60 and which the user partly grips into when he is to hold the instrument. In the example of FIG. 15a the said hole 64 is placed at the back end of the handle 40.

FIGS. 16 and 17 show an instrument with a two legged handle where respective aide surfaces 29 and 30 form convex surfaces. The head portion thereby approximately acquires a cigar shape, as is especially evident from FIG. 17.

It is evident that all of the cleaning instruments with a one-legged handle, see the FIGS. 7–15, comprise a larger front open portion 66 which is surrounded by the front part of the handle, the middle portion-leg and the head member 12 projecting forwardly from there. On this point they resemble the construction with two legs. The large opening 66 functions so that when the user places the instrument backwards towards the root of the tongue, the front parts of the tongue can partially extend through is the opening 66. If the opening 66 became "closed" by a sheet material, this would prevent the flexible use of the instrument according to the invention.

The cleaning instrument which is show in the enclosed Figures and discussed in the foregoing can preferably be made of a suitable plastic material, chat is to say plastic materials which are usually used in the manufacture of toothbrushes and similar instruments. However it is also possible to make the cleaning instrument of metals, but plastic materials are preferred.

With the described construction of the instrument according to the invention for cleaning of the regions within the oral cavity, the features can now be combined which apply to the loosening and thereafter the scraping of material which in collected in various parts of the oral cavity and which creates bad breath. Thus this constitutes a big improvement relative to the previously known instruments.

What is claimed is:

1. A cleaning instrument for an oral cavity comprising
   a cleaning member having an upper surface, an oppositely disposed lower surface and a scraping edge extending along an edge of said lower surface for scraping of at least one of a tongue and an interior surface of an oral cavity, said scraping edge being a ridge disposed along a rear edge of said cleaning member and in upstanding relation to said lower surface, said ridge having a rounded apex,
   a plurality of bristles mounted in said upper surface of said cleaning member; and
   at least one handle connected to a rear of said cleaning member for manipulating said cleaning member within an oral cavity.

2. A cleaning instrument as set forth in claim 1 wherein said ridge extends from said lower surface a distance of from 1 to 3 millimeters.

3. A cleaning instrument as set forth in claim 1 wherein each of said upper surface and lower surface is convex in a longitudinal direction thereof.

4. A cleaning instrument as set forth in claim 1 wherein said cleaning member is straight and is disposed transversely of said handle.

5. A cleaning instrument as set forth in claim 1 wherein said cleaning member is bow shaped and said bristles are disposed in an arcuate manner.

6. A cleaning instrument as set forth in claim 5 which further comprises a pair of said handles, each said handle being secured to an apposite end of said cleaning member from the other of said handles.

7. A cleaning instrument as set forth in claim 5 which further comprises a pair of spaced apart legs connected to and between said handle and said cleaning member.

8. A cleaning instrument as set forth in claim 1 wherein said bristles have a height of up to 8 millimeters.

9. A cleaning instrument as set forth in claim 1 wherein said bristles include bristles of dissimilar hardness.

10. A cleaning instrument as set forth in claim 1 wherein said cleaning member has a pair of oppositely disposed side walls extending between said upper surface and said lower surface.

11. A cleaning instrument as set forth in claim 10 wherein said cleaning member has a rectangular cross-section with rounded corners.

* * * * *

UNITED STATES PATENT AND TRADEMARK OFFICE
CERTIFICATE OF CORRECTION

PATENT NO.     : 6,289,545 B1                                    Page 1 of 1
DATED          : September 18, 2001
INVENTOR(S)    : Olav Molster It is certified that error appears in the above-identified patent and that said Letters Patent is hereby corrected as shown below:

<u>Title page,</u>
Delete "[*] Notice: This patent is subject to a terminal disclaimer".

Signed and Sealed this

Twenty-fifth Day of June, 2002

Attest:

Attesting Officer

JAMES E. ROGAN
*Director of the United States Patent and Trademark Office*